United States Patent [19]

Chu et al.

[11] 4,278,827

[45] Jul. 14, 1981

[54] SHAPE SELECTIVE REACTIONS WITH ZEOLITE CATALYST MODIFIED WITH GROUP IVB METAL

[75] Inventors: Chin-Chiun Chu, North Brunswick; Warren W. Kaeding, Westfield, both of N.J.

[73] Assignee: Mobil Oil Corporation, New York, N.Y.

[21] Appl. No.: 137,881

[22] Filed: Apr. 7, 1980

[51] Int. Cl.³ .................. C07C 2/68; C07C 5/22; C07C 5/52
[52] U.S. Cl. .................. 585/467; 585/470; 585/474; 585/475
[58] Field of Search ............... 585/467, 474, 475, 470

[56] References Cited

U.S. PATENT DOCUMENTS

| | | | |
|---|---|---|---|
| 3,965,208 | 6/1976 | Butter et al. | 585/454 |
| 3,972,832 | 8/1976 | Butter et al. | 585/514 |
| 3,979,472 | 9/1976 | Butter | 585/408 |
| 4,002,697 | 1/1977 | Chen | 585/467 |
| 4,034,053 | 7/1977 | Kaeding et al. | 585/467 |
| 4,052,476 | 10/1977 | Morrison | 585/475 |
| 4,067,920 | 1/1978 | Kaeding | 585/467 |
| 4,101,597 | 7/1978 | Breckenridge | 585/475 |
| 4,117,026 | 9/1978 | Haag et al. | 585/475 |
| 4,128,592 | 12/1978 | Kaeding | 585/467 |
| 4,137,195 | 1/1979 | Chu | 252/437 |

*Primary Examiner*—Curtis R. Davis
*Attorney, Agent, or Firm*—C. A. Huggett; M. G. Gilman; R. J. Cier

[57] ABSTRACT

A process for the conversion of aromatic compounds to dialkylbenzene compounds rich in the 1,4-dialkylbenzene isomer. The reaction is carried out in the presence of a particular type of zeolite catalyst having a silica to alumina mole ratio of at least 12 and a constraint index of about 1-12, said catalyst having been modified by treatment with compounds of germanium, tin and/or lead, and optionally phosphorus, to deposit a minor proportion of such elements on the zeolite.

26 Claims, No Drawings

4,278,827

SHAPE SELECTIVE REACTIONS WITH ZEOLITE CATALYST MODIFIED WITH GROUP IVB METAL

BACKGROUND OF THE INVENTION

1. Field of the Invention

The invention disclosed herein relates to the production of dialkylbenzene compounds utilizing a modified crystalline zeolite catalyst to yield a product mixture in which the 1,4-dialkylbenzene isomer is substantially in excess of its normal equilibrium concentration.

2. Description of the Prior Art

The disproportionation of aromatic hydrocarbons in the presence of zeolite catalysts has been described by Grandio et al. in the OIL AND GAS JOURNAL, Vol. 69, Number 48(1971).

U.S. Pat. Nos. 3,126,422; 3,413,374; 3,598,878; 3,598,879 and 3,607,961 show vapor-phase disproportionation of toluene over various catalysts.

In these prior art processes, the dimethylbenzene product produced has the equilibrium composition of approximately 24 percent of 1,4-, 54 percent of 1,3- and 22 percent of 1,2-isomer. Of the dimethylbenzene isomers, 1,3-dimethylbenzene is normally the least desired product, with 1,2- and 1,4-dimethylbenzene being the more useful products. 1,4-Dimethylbenzene is of particular value, being useful in the manufacture of terephthalic acid which is an intermediate in the manufacture of synthetic fibers such as "Dacron". Mixtures of dimethylbenzene isomers, either alone or in further admixture with ethylbenzene, have previously been separated by expensive superfractionation and multistage refrigeration steps. Such process, as will be realized, involves high operation costs and has a limited yield.

Various modified zeolite catalysts have been developed to alkylate or disproportionate toluene with a greater or lesser degree of selectivity to 1,4-dimethylbenzene isomer. Hence, U.S. Pat. Nos. 3,972,832, 4,034,053, 4,128,592 and 4,137,195 disclose particular zeolite catalysts which have been treated with compounds of phosphorus and/or magnesium. Boron-containing zeolites are shown in U.S. Pat. No. 4,067,920 and antimony-containing zeolites in U.S. Pat. No. 3,979,472. Similarly, U.S. Pat. Nos. 3,965,208 and 4,117,026 disclose other modified zeolites useful for shape selective reactions.

While the above-noted prior art is considered of interest in connection with the subject matter of the present invention, the conversion process described herein, utilizing a crystalline zeolite catalyst of specified characteristics which has undergone the particular treatment disclosed, has not, insofar as is known, been previously described.

SUMMARY OF THE INVENTION

In accordance with the present invention, there has now been discovered a novel process for conversion of organic compounds (e.g., hydrocarbon compounds) in the presence of a particular type of modified zeolite catalyst. An especially advantageous element of the invention comprises the selective production of the 1,4-isomer of dialkylated benzene compounds. The process involves contacting an alkylated aromatic compound, either alone or in admixture with a suitable alkylating agent such as methanol or ethylene, with particular type of modified crystalline zeolite catalyst and under suitable conversion conditioning to effect disproportionation or transalkylation of alkylbenzene compounds or alkylation of aromatic compounds to selectively produce the 1,4-dialkylbenzene isomer in excess of its normal equilibrium concentration.

The particular type of crystalline zeolite catalysts utilized herein are zeolite materials having a silica to alumina ratio of at least about 12, a constraint index within the approximate range of 1 to 12 and which have been modified by initial treatment with a compound derived from one or more of the metals of Group IVB of the Periodic Table of Elements (i.e. Ge, Sn and Pb) to yield a composite containing a minor proportion of an oxide of such metal. In addition to treatment of the zeolite with the germanium, tin or lead containing compound, the zeolite may also be treated with a phosphorus-containing compound to deposit a minor proportion of an oxide of phosphorus thereon in addition to the oxide of the Group IVB metal.

An embodiment of the disclosed invention is a process for the alkylation of aromatic compounds, in the presence of the herein described modified zeolite catalysts, with selective production of the 1,4-dialkylbenzene isomer in preference to the 1,2- and 1,3-isomers thereof. Especially preferred embodiments involve the selective production of 1,4-dimethylbenzene from toluene and methanol and 1-ethyl-4-methylbenzene from toluene and ethylene.

Another embodiment contemplates the selective disproportionation or transalkylation of alkylbenzene and polyalkylbenzene compounds in the presence of the disclosed catalysts, thereby yielding 1,4-disubstituted benzenes in excess of their normal equilibrium concentration. For example, under appropriate conditions of temperature and pressure, toluene will disproportionate in the presence of these catalysts to produce benzene and dimethylbenzenes rich in the desirable 1,4-isomer.

DESCRIPTION OF SPECIFIC EMBODIMENTS

The crystalline zeolites utilized herein are members of a novel class of zeolitic materials which exhibit unusual properties. Although these zeolites have unusually low alumina contents, i.e. high silica to alumina mole ratios, they are very active even when the silica to alumina mole ratio exceeds 30. The activity is surprising since catalytic activity is generally attributed to framework aluminum atoms and/or cations associated with these aluminum atoms. These zeolites retain their crystallinity for long periods in spite of the presence of steam at high temperature which induces irreversible collapse of the framework of other zeolites, e.g. of the X and A type. Furthermore, carbonaceous deposits, when formed, may be removed by burning at higher than usual temperatures to restore activity. These zeolites, used as catalysts, generally have low coke-forming activity and therefore are conducive to long times on stream between regenerations by burning carbonaceous deposits with oxygen-containing gas such as air.

An important characteristic of the crystal structure of this novel class of zeolites is that it provides a selective constrained access to and egress from the intracrystalline free space by virtue of having an effective pore size intermediate between the small pore Linde A and the large pole Linde X, i.e. the pore windows of the structure are of about a size such as would be provided by 10-membered rings of silicon atoms interconnected by oxygen atoms. It is to be understood, of course, that these rings are those formed by the regular disposition of the tetrahedra making up the anionic framework of the crystalline zeolite, the oxygen atoms themselves being bonded to the silicon (or aluminum, etc.) atoms at the centers of the tetrahedra.

The silica to alumina mole ratio referred to may be determined by conventional analysis. This ratio is meant to represent, as closely as possible, the ratio in the rigid anionic framework of the zeolite crystal and to exclude aluminum in the binder or in cationic or other form within the channels. Although zeolites with a silica to alumina mole ratios of at least 12 are useful, it is preferred in some instances to use zeolites having substantially higher silica/alumina ratios, e.g. 1600 and above. In addition, zeolites as otherwise characterized herein but which are substantially free of aluminum, that is zeolites having silica to alumina mole ratios of up to infinity, are found to be useful and even preferable in some instances. Such "high silica" or "highly siliceous" zeolites are intended to be included within this description. Also to be included within this definition are substantially pure silica analogs of the useful zeolites described herein, that is to say those zeolites having no measurable amount of aluminum (silica to alumina mole ratio of infinity) but which otherwise embody the characteristics disclosed.

The novel class of zeolites, after activation, acquire an intracrystalline sorption capacity for normal hexane which is greater than that for water, i.e. they exhibit "hydrophobic" properties. This hydrophobic character can be used to advantage in some applications.

The novel class of zeolites useful herein have an effective pore size such as to freely sorb normal hexane. In addition, the structure must provide constrained access to larger molecules. It is sometimes possible to judge from a known crystal structure whether such constrained access exists. For example, if the only pore windows in a crystal are formed by 8-membered rings of silicon and aluminum atoms, then access by molecules of larger cross-section than normal hexane is excluded and the zeolite is not of the desired type. Windows of 10-membered rings are preferred, although in some instances excessive puckering of the rings or pore blockage may render these zeolites ineffective.

Although 12-membered rings in theory would not offer sufficient constraint to produce advantageous conversions, it is noted that the puckered 12-ring structure of TMA offretite does show some constrained access. Other 12-ring structures may exist which may be operative for other reasons and, therefore, it is not the present intention to entirely judge the usefulness of a particular zeolite solely from theoretical structural considerations.

Rather than attempt to judge from crystal structure whether or not a zeolite possesses the necessary constrained access to molecules of larger cross-section than normal paraffins, a simple determination of the "Constraint Index" as herein defined may be made by passing continuously a mixture of an equal weight of normal hexane and 3-methylpentane over a sample of zeolite at atmospheric pressure according to the following procedure. A sample of the zeolite, in the form of pellets or extrudate, is crushed to a particle size about that of coarse sand and mounted in a glass tube. Prior to testing, the zeolite is treated with a stream of air at 540° C. for at least 15 minutes. The zeolite is then flushed with helium and the temperature is adjusted between 290° C. and 510° C. to give an overall conversion of between 10% and 60%. The mixture of hydrocarbons is passed at 1 liquid hourly space velocity (i.e., 1 volume of liquid hydrocarbon per volume of zeolite per hour) over the zeolite with a helium dilution to give a helium to (total) hydrocarbon mole ratio of 4:1. After 20 minutes on stream, a sample of the effluent is taken and analyzed, most conveniently by gas chromatography, to determine the fraction remaining unchanged for each of the two hydrocarbons.

While the above experimental procedure will enable one to achieve the desired overall conversion of 10 to 60% for most zeolite samples and represents preferred conditions, it may occasionally be necessary to use somewhat more severe conditions for samples of very low activity, such as those having an exceptionally high silica to alumina mole ratio. In those instances, a temperature of up to about 540° C. and a liquid hourly space velocity of less than one, such as 0.1 or less, can be employed in order to achieve a minimum total conversion of about 10%.

The "Constraint Index" is calculated as follows:

$$\text{Constraint Index} = \frac{\log_{10} (\text{fraction of hexane remaining})}{\log_{10} (\text{fraction of 3-methylpentane remaining})}$$

The Constraint Index approximates the ratio of the cracking rate constants for the two hydrocarbons. Zeolites suitable for the present invention are those having a Constraint Index of 1 to 12. Constraint Index (CI) values for some typical materials are:

|  | C.I. |
| --- | --- |
| ZSM-4 | 0.5 |
| ZSM-5 | 8.3 |
| ZSM-11 | 8.7 |
| ZSM-12 | 2 |
| ZSM-23 | 9.1 |
| ZSM-35 | 4.5 |
| ZSM-38 | 2 |
| ZSM-48 | 3.4 |
| TMA Offretite | 3.7 |
| Clinoptilolite | 3.4 |
| Beta | 0.6 |
| H-Zeolon (mordenite) | 0.4 |
| REY | 0.4 |
| Amorphous Silica-Alumina | 0.6 |
| Erionite | 38 |

The above-described Constraint Index is an important and even critical definition of those zeolites which are useful in the instant invention. The very nature of this parameter and the recited technique by which it is determined, however, admit of the possibility that a given zeolite can be tested under somewhat different conditions and thereby exhibit different Constraint Indices. Constraint Index seems to vary somewhat with severity of operation (conversion) and the presence or absence of binders. Likewise, other variables such as crystal size of the zeolite, the presence of occluded contaminants, etc., may affect the constraint index. Therefore, it will be appreciated that it may be possible to so select test conditions as to establish more than one value in the range of 1 to 12 for the Constraint Index of a particular zeolite. Such a zeolite exhibits the constrained access as herein defined and is to be regarded as having a Constraint Index in the range of 1 to 12. Also contemplated herein as having a Constraint Index in the range of 1 to 12 and therefore within the scope of the defined novel class of highly siliceous zeolites are those zeolites which, when tested under two or more sets of conditions within the above-specified ranges of temperature and conversion, produce a value of the Constraint Index slightly less than 1, e.g. 0.9, or somewhat greater than 12, e.g. 14 or 15, with at least one other value within the range of 1 to 12. Thus, it should be understood that the Constraint Index value as used herein is an inclusive rather than an exclusive value. That is, a crystalline zeolite when identified by any combination of conditions within the testing definition set forth herein as having a Constraint Index in the range of 1 to 12 is intended to be included in the instant novel zeolite definition whether or not the same identical zeolite, when tested under other of the defined conditions, may give a Constraint Index value outside of the range of 1 to 12.

The novel class of zeolites defined herein is exemplified by ZSM-5, ZSM-11, ZSM-12, ZSM-23, ZSM-35, ZSM-38, ZSM-48 and other similar materials.

ZSM-5 is described in greater detail in U.S. Pat. No. 3,702,886 and No. Re 29,948. The entire descriptions contained within those patents, particularly the X-ray diffraction pattern of therein disclosed ZSM-5, are incorporated herein by reference.

ZSM-11 is described in U.S. Pat. No. 3,709,979. That description, and in particular the X-ray diffraction pattern of said ZSM-11, is incorporated herein by reference.

ZSM-12 is described in U.S. Pat. No. 3,832,449. That description, and in particular the X-ray diffraction pattern disclosed therein, is incorporated herein by reference.

ZSM-23 is described in U.S. Pat. No. 4,076,842. The entire content thereof, particularly the specification of the X-ray diffraction pattern of the disclosed zeolite, is incorporated herein by reference.

ZSM-35 is described in U.S. Pat. No. 4,016,245. The description of that zeolite, and particularly the X-ray diffraction pattern thereof, is incorporated herein by reference.

ZSM-38 is more particularly described in U.S. Pat. No. 4,046,859. The description of that zeolite, and particularly the specified X-ray diffraction pattern thereof, is incorporated herein by reference.

ZSM-48 can be identified, in terms of moles of anhydrous oxides per 100 moles of silica, as follows:

(0–15)RN:(0–1.5)M$_{2/n}$O:(0–2)Al$_2$O$_3$:(100)SiO$_2$ wherein M is at least one cation having a valence n; and RN is a C$_1$–C$_{20}$ organic compound having at least one amine functional group of pK$_a \geq 7$.

It is recognized that, particularly when the composition contains tetrahedral, framework aluminum, a fraction of the amine functional groups may be protonated. The doubly protonated form, in conventional notation, would be (RNH)$_2$O and is equivalent in stoichiometry to 2RN+H$_2$O.

The characteristic X-ray diffraction pattern of the synthetic zeolite ZSM-48 has the following significant lines:

| Characteristic Lines of ZSM-48 | |
| --- | --- |
| d(A) | Relative Intensity |
| 11.9 | W–S |
| 10.2 | W |
| 7.2 | W |
| 5.9 | W |
| 4.2 | VS |
| 3.9 | VS |
| 3.6 | W |

| -continued | |
| --- | --- |
| Characteristic Lines of ZSM-48 | |
| d(A) | Relative Intensity |
| 2.85 | W |

These values were determined by standard techniques. The radiation was the K-alpha doublet of copper, and a scintillation counter spectrometer with a strip chart pen recorder was used. The peak heights, I, and the positions as a function of 2 times theta, where theta is the Bragg angle, were read from the spectrometer chart. From these, the relative intensities, 100 I/I$_o$, where I$_o$ is the intensity of the strongest line or peak, and d (obs.), the interplanar spacing in A, corresponding to the recorded lines, were calculated. In the foregoing table the relative intensities are given in terms of the symbols W=weak, VS=very strong and W-S=weak-to-strong. Ion exchange of the sodium ion with cations reveals substantially the same pattern with some minor shifts in interplanar spacing and variation in relative intensity. Other minor variations can occur depending on the silicon to aluminum ratio of the particular sample, as well as if it has been subjected to thermal treatment.

The ZSM-48 can be prepared from a reaction mixture containing a source of silica, water, RN, an alkali metal oxide (e.g. sodium) and optionally alumina. The reaction mixture should have a composition, in terms of mole ratios of oxides, falling within the following ranges:

| Reactants | | Broad | Preferred |
| --- | --- | --- | --- |
| Al$_2$O$_3$/SiO$_2$ | = | 0 to 0.02 | 0 to 0.01 |
| Na/SiO$_2$ | = | 0 to 2 | 0.1 to 1.0 |
| RN/SiO$_2$ | – | 0.01 to 2.0 | 0.05 to 1.0 |
| OH$^-$/SiO$_2$ | = | 0 to 0.25 | 0 to 0.1 |
| H$_2$O/SiO$_2$ | = | 10 to 100 | 20 to 70 |
| H$^+$(added)/SiO$_2$ | = | 0 to 0.2 | 0 to 0.05 | where RN is a C$_1$–C$_{20}$ organic compound having amine functional group of pK$_a \geq 7$. The mixture is maintained at 80°–250° C. until crystals of the material are formed. H$^+$(added) is moles acid added in excess of the moles of hydroxide added. In calculating H$^+$(added) and OH values, the term acid (H$^+$) includes both hydronium ion, whether free or coordinated, and aluminum. Thus aluminum sulfate, for example, would be considered a mixture of aluminum oxide, sulfuric acid, and water. An amine hydrochloride would be a mixture of amine and HCl. In preparing the highly siliceous form of ZSM-48 no alumina is added. Thus, the only aluminum present occurs as an impurity in the reactants.

Preferably, crystallization is carried out under pressure in an autoclave or static bomb reactor, at 80° C. to 250° C. Thereafter, the crystals are separated from the liquid and recovered. The composition can be prepared utilizing materials which supply the appropriate oxide. Such compositions include sodium silicate, silica hydrosol, silica gel, silicic acid, RN, sodium hydroxide, sodium chloride, aluminum sulfate, sodium aluminate, aluminum oxide, or aluminum itself. RN is a C$_1$–C$_{20}$ organic compound containing at least one amine functional group of pK$_a \geq 7$, as defined above, and includes such compounds as C$_3$–C$_{18}$ primary, secondary, and tertiary amines, cyclic amine (such as piperidine, pyrrolidine and piperazine), and polyamines such as NH$_2$—C$_n$H$_{2n}$—NH$_2$ wherein n is 4–12.

The original cations can be subsequently replaced, at least in part, by calcination and/or ion exchange with another cation. Thus, the original cations are exchanged into a hydrogen or hydrogen ion precursor form or a form in which the original cations has been replaced by a metal of Groups II through VIII of the Periodic Table. Thus, for example, it is contemplated to exchange the original cations with ammonium ions or with hydronium ions. Catalytically active forms of these would include, in particular, hydrogen, rare earth metals, aluminum, manganese and other metals of Groups II and VIII of the Periodic Table.

It is to be understood that by incorporating by reference the foregoing patents to describe examples of specific members of the novel class with greater particularity, it is intended that identification of the therein disclosed crystalline zeolites be resolved on the basis of their respective X-ray diffraction patterns. As discussed above, the present invention contemplates utilization of such catalysts wherein the mole ratio of silica to alumina is essentially unbounded. The incorporation of the identified patents should therefore not be construed as limiting the disclosed crystalline zeolites to those having the specific silica-alumina mole ratios discussed therein, it now being known that such zeolites may be substantially aluminum-free and yet, having the same crystal structure as the disclosed materials, may be useful or even preferred in some applications. It is the crystal structure, as identified by the X-ray diffraction "fingerprint", which establishes the identity of the specific crystalline zeolite material.

The specific zeolites described, when prepared in the presence of organic cations, are substantially catalytically inactive, possibly because the intracrystalline free space is occupied by organic cations from the forming solution. They may be activated by heating in an inert atmosphere at 540° C. for one hour, for example, followed by base exchange with ammonium salts followed by calcination at 540° C. in air. The presence of organic cations in the forming solution may not be absolutely essential to the formation of this type zeolite; however, the presence of these cations does appear to favor the formation of this special class of zeolite. More generally, it is desirable to activate this type catalyst by base exchange with ammonium salts followed by calcination in air at about 540° C. for from about 15 minutes to about 24 hours.

Natural zeolites may sometimes be converted to zeolite structures of the class herein identified by various activation procedures and other treatments such as base exchange, steaming, alumina extraction and calcination, alone or in combinations. Natural minerals which may be so treated include ferrierite, brewsterite, stilbite, dachiardite, epistilbite, heulandite, and clinoptilolite.

The preferred crystalline zeolites for utilization herein include ZSM-5, ZSM-11, ZSM-12, ZSM-23, ZSM-35, ZSM-38, and ZSM-48, with ZSM-5 being particularly preferred.

In a preferred aspect of this invention, the zeolites hereof are selected as those providing among other things a crystal framework density, in the dry hydrogen form, of not less than about 1.6 grams per cubic centimeter. It has been found that zeolites which satisfy all three of the discussed criteria are most desired for several reasons. When hydrocarbon products or by-products are catalytically formed, for example, such zeolites tend to maximize the production of gasoline boiling range hydrocarbon products. Therefore, the preferred zeolites useful with respect to this invention are those having a Constraint Index as defined above of about 1 to about 12, a silica to alumina mole ratio of at least about 12 and a dried crystal density of not less than about 1.6 grams per cubic centimeter. The dry density for known structures may be calculated from the number of silicon plus aluminum atoms per 1000 cubic Angstroms, as given, e.g., on Page 19 of the article ZEOLITE STRUCTURE by W. M. Meier. This paper, the entire contents of which are incorporated herein by reference, is included in PROCEEDINGS OF THE CONFERENCE ON MOLECULAR SIEVES, (London, April 1967) published by the Society of Chemical Industry, London, 1968.

When the crystal structure is unknown, the crystal framework density may be determined by classical pycnometer techniques. For example, it may be determined by immersing the dry hydrogen form of the zeolite in an organic solvent which is not sorbed by the crystal. Or, the crystal density may be determined by mercury porosimetry, since mercury will fill the interstices between crystals but will not penetrate the intracrystalline free space.

It is possible that the unusual sustained activity and stability of this special class of zeolites is associated with its high crystal anionic framework density of not less than about 1.6 grams per cubic centimeter. This high density must necessarily be associated with a relatively small amount of free space within the crystal, which might be expected to result in more stable structures. This free space, however, is important as the locus of catalytic activity.

Crystal framework densities of some typical zeolites, including some which are not within the purview of this invention, are:

|  | Void Volume | Framework Density |
| --- | --- | --- |
| Ferrierite | 0.28 cc/cc | 1.76 g/cc |
| Mordenite | .28 | 1.7 |
| ZSM-5, -11 | .29 | 1.79 |
| ZSM-12 | — | 1.8 |
| ZSM-23 | — | 2.0 |
| Dachiardite | .32 | 1.72 |
| L | .32 | 1.61 |
| Clinoptilolite | .34 | 1.71 |
| Laumontite | .34 | 1.77 |
| ZSM-4 (Omega) | .38 | 1.65 |
| Heulandite | .39 | 1.69 |
| P | .41 | 1.57 |
| Offretite | .40 | 1.55 |
| Levynite | .40 | 1.54 |
| Erionite | .35 | 1.51 |
| Gmelinite | .44 | 1.46 |
| Chabazite | .47 | 1.45 |
| A | .5 | 1.3 |
| Y | .48 | 1.27 |

When synthesized in the alkali metal form, the zeolite is conveniently converted to the hydrogen form, generally by intermediate formation of the ammonium form as a result of ammonium ion exchange and calcination of the ammonium form to yield the hydrogen form. In addition to the hydrogen form, other forms of the zeolite wherein the original alkali metal has been reduced to less than about 1.5 percent by weight may be used. Thus, the original alkali metal of the zeolite may be replaced by ion exchange with other suitable metal cations of Groups I through VIII of the Periodic Table, including, by way of example, nickel, copper, zinc, palladium, calcium or rare earth metals. In practicing a particularly desired chemical conversion process, it may be useful to incorporate the above-described crystalline zeolite with a matrix comprising another material resistant to the temperature and other conditions employed in the process. Such matrix material is useful as a binder and imparts greater resistance to the catalyst for the severe temperature, pressure and reactant feed stream velocity conditions encountered in many cracking processes.

Useful matrix materials include body synthetic and naturally occurring substances, as well as inorganic materials such as clay, silica and/or metal oxides. The latter may be either naturally occurring or in the form of gelatinous precipitates or gels including mixtures of silica and metal oxides. Naturally occurring clays which can be composited with the zeolite include those of the montmorillonite and kaolin families, which families include the sub-bentonites and the kaolins commonly known as Dixie, McNamee-Georgia and Florida clays or others in which the main mineral constituent is halloysite, kaolinite, dickite, nacrite or anauxite. Such clays can be used in the raw state as originally mined or initially subjected to calcination, acid treatment or chemical modification.

In addition to the foregoing materials, the zeolites employed herein may be composited with a porous matrix material, such as alumina, silica-alumina, silica-magnesia, silica-zirconia, silica-thoria, silica-beryllia, and silica-titania, as well as ternary compositions, such as silica-alumina-thoria, silica-alumina-zirconia, silica-alumina-magnesia and silica-magnesia-zirconia. The matrix may be in the form of a cogel. The relative proportions of zeolite component and inorganic oxide gel matrix, on an anhydrous basis, may vary widely with the zeolite content ranging from between about 1 to about 99 percent by weight and more usually in the range of about 5 to about 80 percent by weight of the dry composite.

The above crystalline zeolites employed are, in accordance with the present invention, contacted with a solution of one or more compounds of the metals of Group IVB of the Periodic Chart of the Elements. The Periodic Chart referred to herein is that version officially approved and adopted by the United States National Bureau of Standards (NBS) and the International Union of Pure and Applied Chemists (IUPAC), the contemplated elements of Group IVB being germanium (Ge), tin (Sn) and lead (Pb).

Solutions of such compounds may be in any suitable solvent which is inert with respect to the metal-containing compound and the zeolite. Non-limiting examples of some suitable solvents include water, aliphatic and aromatic hydrocarbons, alcohols, organic acids (such as acetic acid, formic acid, propionic acid and so forth), and inorganic acids (such as hydrochloric acid, sulfuric acid and nitric acid). Other commonly available solvents such as halogenated hydrocarbons, ketones, ethers, etc. may be useful to dissolve some metal compounds or complexes. Generally, the most useful solvent will be found to be water. However, the solvent of choice for any particular compound will, of course, be determined by the nature of that compound and for that reason the foregoing list should not be considered exhaustive of all of the suitable possibilities.

Representative germanium-containing compounds include germanium dichloride, germanium tetrachloride, germanium dibromide, germanium tetrabromide, germanium di- and tetra- fluorides and iodides, germanium oxide, germanium sulfide, trimethylgermanium, triethylgermanium, and germanium oxychloride. This listing is not to be taken as encompassing all of the utilizable germanium containing compounds. It is merely intended to be illustrative of some of the representative metal compounds which those in the art will find useful in practicing the disclosed invention. The knowledgeable reader will readily appreciate that there are numerous other known germanium salts and complexes which would prove useful herein to provide solutions containing germanium suitable for combination with the zeolite in the manner hereinafter described.

Reaction of the zeolite with the treating germanium compound is effected by contacting the zeolite with such compound. Where the treating compound is a liquid, such compound can be in solution in a solvent at the time contact with the zeolite is effected. Any solvent relatively inert with respect to the treating germanium compound and the zeolite may be employed. Suitable solvents include water and aliphatic, aromatic or alcoholic liquid. The treating compound may also be used without a solvent, i.e. may be used as a neat liquid. Where the treating compound is in the gaseous phase, it can be used by itself or in admixture with a gaseous diluent relatively inert to the treating compound and the zeolite (such as helium or nitrogen) or with an organic solvent such as octane or toluene. Heating of the germanium compound impregnated catalyst subsequent to preparation and prior to use is preferred, and heating can, if desired, be carried out in the presence of oxygen—for example, in air. Although heating may be carried out at a temperature of about 150° C. or more, higher temperatures, e.g. up to about 500° C., are preferred. Heating is generally carried out for 1-5 hours but may be extended to 24 hours or longer. While heating temperatures above about 500° C. may be employed, they are generally not necessary, and at temperatures of about 1000° C. the crystal structure of the zeolite tends to deteriorate. After heating in air at elevated temperatures, and without being limited by any theoretical considerations, it is contemplated that the germanium is actually present in the zeolite in an oxidized state, such as $GeO_2$.

The amount of germanium dioxide incorporated in the zeolite should be at least about 0.25 percent by weight. However, it is preferred that the amount utilized comprise at least about 1.0 percent by weight, particularly when the zeolite is combined with a binder, e.g. 35 weight percent of alumina. The amount of germanium dioxide can be as high as about 30 percent by weight or more, depending on the amount and type of binder present. Preferably, the amount of oxide added to the zeolite will be between about 1 and about 15 percent by weight.

The amount of germanium incorporated with the zeolite by reaction with elemental germanium or germanium-containing compound will depend upon several factors. One of these is the reaction time, i.e., the time that the zeolite and the germanium-containing source are maintained in contact with each other. With greater reaction times, all other factors being equal, a greater amount of metal is incorporated with the zeolite. Other factors upon which the amount of germanium incorporated with the zeolite is dependent include reaction temperature, concentration of the treating compound in the reaction mixture, the degree to which the zeolite has been dried prior to reaction with the metal-containing compound, the conditions of drying of the zeolite after reaction with the treating compound, and the amount and type of binder incorporated with the zeolite.

Oxides of tin are also effective modifying components for imparting the desirable shape selective activity to the particular type of zeolites disclosed. Examples of representative tin-containing compounds suitable for deposition of that metal on the zeolite include tin metal, tin acetate, tin bromide, tin chloride, tin fluoride, tin iodide, tin nitrate, tin oxide, tin sulfide, tin sulfur chloride, tin sulfate, and tin tartarate. As discussed above with respect to the illustrative listing of germanium compounds, the foregoing is not to be considered as an exhaustive list of the utilizable tin salts and complexes. There are numerous tin compounds which the foregoing will suggest to those skilled in the art as being suitable for providing the tin-containing solutions for treatment of the zeolite as hereinafter described.

Reaction of the zeolite with the tin compounds is accomplished in substantially the same way as that recited above with respect to the germanium-containing compounds. Without being limited by any theoretical considerations, it is contemplated that the tin is likewise in an oxidized state, such as $SnO_2$.

The amount of tin oxide incorporated in the zeolite should be at least about 0.25 percent by weight. However, it is preferred that the amount utilized comprise at least about 1.0 percent by weight, particularly when the zeolite is combined with a binder, e.g. 35 weight percent of alumina. The amount of tin oxide can be as high as about 30 percent by weight or more depending on the amount and type of binder present. Preferably, the amount of tin oxide added to the zeolite is between about 1 and about 25 percent by weight.

Oxides of lead may also be employed as a modifying component. The lead oxide is contemplated as being present as PbO alone or in combination with other compounds of lead in an oxidized state. In all instances, regardless of the particular state of oxidation of the lead, its content with respect to the zeolite is computed as if it were present as PbO. Generally, the amount of PbO in the composite catalyst will be between about 0.25 and about 45 weight percent, and preferably between about 1.0 and about 40 weight percent, based on the weight of the composite. Reaction of the zeolite with the lead-containing compound is carried out as described above with respect to the treatment with compounds of the element germanium. Examples of lead compounds which may be utilized include lead metal, lead acetate, lead bromide, lead chloride, lead fluoride, lead iodide, lead butyrate, lead carbonate, lead bromate, lead chlorate, lead perchlorate, lead chlorite, lead citrate, lead cyanate, lead cyanide, lead enanthate, lead ethylsulfate, lead formate, lead hydroxide, lead iodate, lead periodate, lead lactate, lead laurate, lead malate, lead oxide, lead nitrate, lead oxychloride, lead palmitate, lead phenolate, lead picrate, lead citrate, lead sulfate, lead sulfide, lead sulfite, lead tartarate, and lead thiocyanate. Again, this listing is not intended to be exhaustive, but rather suggestive to those of skill in the art as to the kinds of metal-containing compounds useful for treating the zeolite as herein described.

In some instances, it may be desirable to modify the crystalline zeolites by combining therewith two or more of the specified metal oxides. Thus, the zeolite may be modified by prior combination therewith of oxides of germanium and tin, oxides of germanium and lead, oxides of tin and lead or even oxides of all three elements. When such modification technique is employed, the respective oxides may be deposited on the zeolite either sequentially or from a solution containing suitable compounds of the elements, the oxides of which are to be combined with the zeolite. The amounts of oxides present in such instance are in the same range as specified above for the individual oxides, with the overall added oxide content being between about 1 and about 40 weight percent of the composite.

A further embodiment of this invention includes additional modification of the above metal oxide-zeolite composites with phosphorus, whereby from about 0.25 weight percent to about 30 weight percent of an oxide of phosphorus, calculated as $P_2O_5$, is combined with the zeolite. The preferred amount of phosphorus oxide will be between about 1.0 weight percent and about 25 weight percent, based on the weight of the treated zeolite. The phosphorus treatment of the zeolite catalyst will preferably be carried out before the previously described modification thereof with Group IVB metals. Reaction of the zeolite compound with the phosphorus-containing compound is carried out essentially as described above with respect to the metal-containing compounds and it is preferred that the total amount of oxides combined with the zeolite, i.e. the phosphorus oxides plus the metal oxides, fall within the approximate range of 2 percent to 35 percent by weight, based on the weight of the treated zeolite.

Representative phosphorus-containing compounds which may be used include derivatives of groups represented by $PX_3$, $RPX_2$, $R_2PX$, $R_3P$, $X_3PO$, $(XO)_3PO$, $(XO)_3P$, $R_3P=O$, $R_3P=S$, $RPO_2$, $RPS_2$, $RP(O)(OX)_2$, $RP(S)(SX)_2$, $R_2P(O)OX$, $R_2P(S)SX$, $RP(SX)_2$, $ROP(OX)_2$, $RSP(SX)_2$, $(RS)_2PSP(SR)_2$, and $(RO)_2POP(OR)_2$, where R is an alkyl or aryl, such as a phenyl radical and X is hydrogen, R, or halide. These compounds include primary, $RPH_2$, secondary, $R_2PH$ and tertiary, $R_3P$, phosphines such as butyl phosphine; the tertiary phosphine oxides $R_3PO$, such as tributylphosphine oxide, the tertiary phosphine sulfides, $R_3PS$, the primary, $RP(O)(OX)_2$, and secondary, $R_2P(O)OX$, phosphonic acids such as benzene phosphonic acid; the corresponding sulfur derivatives such as $RP(S)(SX)_2$ and $R_2P(S)SX$, the esters of the phosphonic acids such as diethyl phosphonate, $(RO)_2P(O)H$, dialkyl alkyl phosphonates, $(RO)_2P(O)R$, and alkyl dialkylphosphinates, $(RO)P(O)R_2$; phosphinous acids, $R_2POX$, such as diethylphosphinous acid, primary, $(RO)P(OX)_2$, secondary, $(RO)_2POX$, and tertiary, $(RO)_3P$, phosphites; and esters thereof such as the monopropyl ester, alkyl dialkylphosphinites, $(RO)PR_2$, and dialkyl alkylphosphinite, $(RO)_2PR$ esters. Corresponding sulfur derivatives may also be employed including $(RS)_2P(S)H$, $(RS)_2P(S)R$, $(RS)P(S)R_2$, $R_2PSX$, $(RS)P(SX)_2$, $(RS)_2PSX$, $(RS)_3P$, $(RS)PR_2$ and $(RS)_2PR$. Examples of phosphite esters include trimethylphosphite, triethylphosphite, diisopropylphosphite, butylphosphite; and pyrophosphites such as tetraethylpyrophosphite. The alkyl groups in the mentioned compounds contain from one to four carbon atoms.

Other suitable phosphorus-containing compounds include the phosphorus halides such as phosphorus trichloride, bromide, and iodide, alkyl phosphorodichloridites, (RO)PCl$_2$, dialkyl phosphorochloridites, (RO)$_2$PCl, dialkylphosphinochloridites, R$_2$PCl, alkyl alkylphosphonochloridates, (RO)(R)P(O)Cl, dialkyl phosphinochloridates, R$_2$P(O)Cl and RP(O)Cl$_2$. Applicable corresponding sulfur derivatives include (RS)PCl$_2$, (RS)$_2$PCl, (RS)(R)P(S)Cl and R$_2$P(S)Cl.

Preferred phosphorus-containing compounds include diphenyl phosphine chloride, trimethylphosphite and phosphorus trichloride, phosphoric acid, phenyl phosphine oxychloride, trimethylphosphate, diphenyl phosphinous acid, diphenyl phosphinic acid, diethylchlorothiophosphate, methyl acid phosphate and other alcohol-P$_2$O$_5$ reaction products.

Particularly preferred are ammonium phosphates, including ammonium hydroen phosphate, (NH$_4$)$_2$HPO$_4$, and ammonium dihydrogen phosphate, NH$_4$H$_2$PO$_4$.

Still another modifying treatment entails steaming of the zeolite by contact with an atmosphere containing from about 5 to about 100 percent steam at a temperature of from about 250° to about 1000° C. for a period of between about 15 minutes and about 100 hours and under pressures ranging from sub-atmospheric to several hundred atmospheres. Preferably, steam treatment is effected at a temperature of between about 400° C. and about 700° C. for a period of between about 1 and about 24 hours.

Another modifying treatment involves precoking of the catalyst to deposit a coating of between about 2 and about 75, and preferably between about 15 and about 75, weight percent of coke therein. Precoking can be accomplished by contacting the catalyst with a hydrocarbon charge, e.g. toluene, under high severity conditions or alternatively at a reduced hydrogen to hydrocarbon concentration, i.e. 0 to 1 mole ratio of hydrogen to hydrocarbon, for a sufficient time to deposit the desired amount of coke thereon.

It is also contemplated that a combination of steaming and precoking of the catalyst under the above conditions may be employed to suitably modify the crystalline zeolite catalyst.

Alkylation of aromatic compounds in the presence of the above-described catalyst is effected by contact of the aromatic with an alkylating agent. A particulary preferred embodiment involves the alkylation of toluene wherein the alkylating agents employed comprise methanol or other well known methylating agents or ethylene. The reaction is carried out at a temperature of between about 250° C. and about 750° C., preferably between about 300° C. and 650° C. At higher temperatures, the zeolites of high silica/alumina ratio are preferred. For example, ZSM-5 having a SiO$_2$/Al$_2$O$_3$ ratio of 30 and upwards is exceptionally stable at high temperatures. The reaction generally takes place at atmospheric pressure, but pressures within the approximate range of 10$^5$ N/m$^2$ to 10$^7$ N/m$^2$ (1–100 atmospheres) may be employed.

Some non-limiting examples of suitable alkylating agents would include olefins such as, for example, ethylene, propylene, butene, decene, and dodecene, as well as formaldehyde, alkyl halides and alcohols, the alkyl portion thereof having from 1 to 16 carbon atoms. Numerous other aliphatic compounds having at least one reactive alkyl radical may be utilized as alkylating agents.

Aromatic compounds which may be selectively alkylated as described herein would include any alkylatable aromatic hydrocarbon such as, for example, benzene, ethylbenzene, toluene, dimethylbenzenes, diethylbenzenes, methylethylbenzenes, propylbenzenes, isopropylbenzenes, isopropylmethylbenzenes, or substantially any mono- or di-substituted benzenes which are alkylatable in the 4-position of the aromatic ring.

The molar ratio of alkylating agent to aromatic compound is generally between about 0.05 and about 5. For instance, when methanol is employed as the methylating agent and toluene is the aromatic, a suitable molar ratio of methanol to toluene has been found to be approximately 1–0.1 moles of methanol per mole of toluene. Reaction is suitably accomplished utilizing a feed weight hourly space velocity (WHSV) of between about 1 and about 1000, and preferably between about 1 and about 200. The reaction product, consisting predominantly of the 1,4-dialkyl isomer, e.g. 1,4-dimethylbenzene, 1-ethyl-4-methylbenzene, etc., or a mixture of the 1,4- and 1,2- isomers together with comparatively smaller amounts of 1,3-dialkylbenzene isomer, may be separated by any suitable means. Such means may include, for example, passing the reaction product stream through a water condenser and subsequently passing the organic phase through a column in which chromatographic separation of the aromatic isomers is accomplished.

When transalkylation is to be accomplished, transalkylating agents are alkyl or polyalkyl aromatic hydrocarbons wherein alkyl may be composed of from 1 to about 5 carbon atoms, such as, for example, toluene, xylene, trimethylbenzene, triethylbenzene, dimethylethylbenzene, ethylbenzene, diethylbenzene, ethyltoluene and so forth.

Another aspect of this invention involves the selective disproportionation of alkylated aromatic compounds to produce dialkylbenzenes wherein the yield of 1,4-dialkyl isomer is in excess of the normal equilibrium concentration. In this context, it should be noted that disproportionation is a special case of transalkylation in which the alkylatable hydrocarbon and the transalkylating agent are the same compound, for example when toluene serves as the donor and acceptor of a transferred methyl group to produce benzene and xylene.

The transalkylation and disproportionation reactions are carried out by contacting the reactants with the above described modified zeolite catalyst at a temperature of between about 350° C. and 750° C. at a pressure of between atmospheric (10$^5$ N/m$^2$) and about 100 atmospheres (10$^7$ N/m$^2$). The reactant feed WHSV will normally fall within the range of about 0.1 to about 50. Preferred alkylated aromatic compounds suitable for utilization in the disproportionation embodiment comprise toluene, ethylbenzene, propylbenzene or substantially any mono-substituted alkylbenzene. These aromatic compounds are selectively converted to, respectively, 1,4-dimethylbenzene, 1,4-diethylbenzene, 1-4-dipropylbenzene, or other 1,4-dialkylbenzene, as appropriate, with benzene being a primary side product in each instance. The product is recovered from the reactor effluent by conventional means, such as distillation to remove the desired products of benzene and dialkylbenzene, and any unreacted aromatic component is recycled for further reaction.

The hydrocarbon conversion processes described herein may be carried out as a batch type, semi-continuous or continuous operation utilizing a fixed or moving bed catalyst system. The catalyst, after use in a moving bed reactor, is conducted to a regeneration zone wherein coke is burned from the catalyst in an oxygen-containing atmosphere (e.g. air) at an elevated temperature, after which the regenerated catalyst is recycled to the conversion zone for further contact with the charge stock. In a fixed bed reactor, regeneration is carried out in a conventional manner where an inert gas containing a small amount of oxygen (0.5-2%) is used to control burning of the coke so as to limit the temperature to a maximum of around 500°-550° C.

The following examples will serve to illustrate certain specific embodiments of the hereindisclosed invention. These examples should not, however, be construed as limiting the scope of the novel invention as there are many variations which may be made thereon without departing from the spirit of the disclosed invention, as those of skill in the art will recognize.

EXAMPLE 1A

[Alkylation reaction with unmodified ZSM-5]

Five grams of HZSM-5 (silica/alumina mole ratio=70; 65% on alumina binder) were placed in a quartz flow reactor and heated to various temperatures between 350° C. and 500° C. A mixture of toluene and methanol, at a 4/1 molar ratio, was passed through the zeolite catalyst at a weight hourly space velocity (WHSV) of 10. The reactor effluent was monitored and the results obtained at the various temperatures are shown below:

| Temperature °C. | Percent Toluene Conversion | Percent para-isomer in Xylenes |
|---|---|---|
| 350 | 47.2 | 24.8 |
| 400 | 58.0 | 24.4 |
| 450 | 68.0 | 24.3 |
| 500 | 87.6 | 24.2 |

EXAMPLE 1B

In a similar manner, toluene was alkylated with ethylene by passing toluene and ethylene, at WHSV of 7.0 and 0.5, respectively, over the unmodified zeolite. The results at various temperatures are shown below:

| Temperature °C. | Percent Toluene Conversion | Isomer ratios of Ethyltoluene | | |
|---|---|---|---|---|
| | | p | m | o |
| 400 | 76.4 | 29.9 | 58.5 | 11.6 |
| 425 | 76.4 | 29.9 | 57.5 | 12.7 |
| 450 | 79.0 | 29.6 | 57.1 | 13.4 |

EXAMPLE 2

[Disproportionation reaction with unmodified ZSM-5]

Toluene was passed over a 6.0 g sample of HZSM-5 ($SiO_2/Al_2O_3$ mole ratio=70; 65% on alumina binder) at a feed WHSV of 3.5-3.6 and at temperatures between 450° C. and 600° C. The results are summarized as follows:

| Temperature °C. | WHSV | Toluene conv., % | % Selectivity, Wt. | | % Para in Xylene Products |
|---|---|---|---|---|---|
| | | | Benzene | Xylenes | |
| 450 | 3.6 | 7.4 | 43.5 | 55.5 | 24.7 |
| 500 | 3.5 | 20.5 | 44.6 | 53.8 | 24.5 |
| 550 | 3.5 | 38.8 | 48.0 | 48.8 | 24.2 |
| 600 | 3.5 | 49.2 | 54.4 | 41.7 | 24.1 |

EXAMPLE 3

[Preparation of Ge-modified zeolite]

A 5.0 g sample of HZSM-5 zeolite was suspended in 10 ml of $GeCl_4$ at ambient temperature for approximately 18 hours. The zeolite was separated by filtration, placed in an oven at 60° C. and heated to 200° C. over a period of 2 hours. The dried zeolite was then calcined at 500° C. for 2 hours. The Ge-ZSM-5 was found to contain 3.05% germanium.

EXAMPLE 4

[Disproportionation reaction with Ge-modified zeolite]

A sample of the Ge-ZSM-5 zeolite of Example 3 was tested for disproportionation of a toluene feed stream. The feed rate (WHSV) was 3.5 and the temperature was varied between 450° C. and 600° C. The results are summarized as follows:

| Temperature °C. | Toluene conv., % | % Selectivity, Wt. | | % Para in Xylene Product |
|---|---|---|---|---|
| | | Benzene | Xylenes | |
| 450 | 0.4 | 71.1 | 25.3 | 32.2 |
| 500 | 0.7 | 64.1 | 35.9 | 32.7 |
| 550 | 1.4 | 56.5 | 43.5 | 30.2 |
| 600 | 3.1 | 52.3 | 46.7 | 28.5 |

By comparison with the results obtained with an unmodified HZSM-5 zeolite [Example 2], it will be seen that the selectivity to the para-isomer in the xylene product has been increased as a result of treating the catalyst with a germanium salt.

EXAMPLE 5

[Alkylation reaction with Ge-modified zeolite]

The Ge-ZSM-5 zeolite of Example 3 was tested for selectivity in the alkylation of aromatics at 400°-450° C. A feed stream consisting of ethylene and toluene was passed over the heated catalyst at WHSV of 0.5 and 7.8, respectively, and the reactor effluent analyzed. The results are outlined below:

| Temp. °C. | Toluene conv., % | % Para Isomer in Ethyltoluene |
|---|---|---|
| 400 | 2.8 | 56.1 |
| 450 | 2.5 | 48.5 |

A very significant increase in selectivity to the para-isomer in the ethyltoluene product is observed relative to that obtained with an unmodified HZSM-5 [Example 1B].

EXAMPLE 6

[Preparation of Sn-modified zeolite]

Ten grams of the ammonium form of ZSM-5 zeolite were placed in a solution of 4.8 g of liquid stannous TEN-CHEM (a tin salt of a mixture of carboxylic acids prepared by Mooney Chemical Inc. and containing 26% Sn) dissolved in 25 ml of glacial acetic acid. The suspension was placed in an oven at about 120° C. to impregnate the zeolite with the tin compound and to remove the acetic acid. The zeolite was thereafter calcined at 500° C. overnight. The tin content of the Sn-ZSM-5 was 10.7 wt. % (calculated).

EXAMPLE 7

[Disproportionation reaction with Sn-modified zeolite]

A stream of toluene was passed over 5.0 g of the Sn-ZSM-5 zeolite of Example 6 at WHSV of 3.5 and at temperatures of between 500° C. and 600° C. The results are summarized as follows:

| Temperature °C. | Toluene conv., % | % Selectivity, mole | | % Para in Xylene Product |
|---|---|---|---|---|
| | | Benzene | Xylenes | |
| 500 | 4.9 | 61.9 | 37.3 | 31.7 |
| 550 | 13.0 | 64.8 | 35.2 | 27.9 |
| 600 | 22.1 | 58.9 | 40.9 | 30.6 |

It is evident from the table that the level of the para-isomer in the xylene product (28–32%) exceeds the equilibrium amount of approximately 24% which had been achieved with the unmodified zeolite (Example 2), thereby demonstrating increased selectivity of the modified catalyst.

EXAMPLE 8

[Preparation of Pb-modified zeolite]

Mixed 3.0 g of HZSM-5 ($SiO_2/Al_2O_3=70$) with a solution of 4.0 g of lead acetate in 8.0 ml of water at 80° C. The mixture was maintained at 80°–90° C. for 2.5 hours and then filtered to recover the zeolite. The recovered zeolite was dried at about 90° C. for 16 hours and then calcined at 500° C. for an additional 2.5 hours to yield 3.72 g of Pb-ZSM-5. The lead content was analyzed to be 30.4 wt. %.

EXAMPLE 9A

[Alkylation reaction with Pb-modified zeolite]

Alkylation of toluene with methanol in the presence of the Pb-modified zeolite catalyst was carried out by passing a feed stream of toluene and methanol (4/1 molar ratio) over the Pb-ZSM-5 of Example 8. The reactor temperature was 500° C. and the feed WHSV was 10. Toluene conversion was 23.6% with a selectivity to the para-isomer in the xylene product of 70.9%, as compared to a para-selectivity of 24.2% for an unmodified ZSM-5 catalyst (Example 1A).

EXAMPLE 9B

In a similar manner, ethylene and toluene were reacted by passing the reactants (at WHSV of 0.5 and 7.0, respectively) over the Pb-ZSM-5 zeolite at 400° C. Conversion of toluene was 13.4% and selectivity to para-isomer in the ethyltoluene product was 85.9%.

With the unmodified zeolite selectivity was 29.9% under similar conditions (Example 1B).

EXAMPLE 10

[Disproportionation reaction with Pb-modified zeolite]

Toluene disproportionation to benzene and xylenes was carried out by passing a stream of toluene over the Pb-ZSM-5 zeolite of Example 8. The reactor temperature was 550° C. and the toluene feed rate (WHSV) was 3.5. Toluene conversion was 5.7% and selectivity to para-xylene was 53.9%, as compared to the equilibrium level of 24.2% para achieved in the presence of an unmodified ZSM-5 (Example 2).

EXAMPLE 11

[Preparation of P-modified zeolite]

200 grams of ammonium-ZSM-5 (65% on alumina binder) were added to a solution of 80 g of diammonium hydrogen phosphate in 300 ml of $H_2O$ at about 90° C. After standing at about 90° C. for 2 hours, the zeolite was filtered, dried at 90° for 2 hours and then calcined at 500° C. for another 2 hours. The recovered P-ZSM-5 zeolite contained 3.43 wt. % phosphorus.

EXAMPLE 12A

[Alkylation reaction with P-modified zeolite]

Alkylation of toluene with methanol was carried out by passing a toluene/methanol feed stream (molar ratio=4/1) over 5.0 g of the P-ZSM-5 zeolite of Example 11. The feed WHSV was 10 and the reactor temperature was varied between 400° C. and 600° C. The results obtained are summarized below:

| Temperature °C. | Percent Toluene Conversion | Percent para-isomer in Xylenes |
|---|---|---|
| 400 | 43.6 | 66.6 |
| 450 | 54.4 | 57.7 |
| 500 | 70.4 | 53.7 |
| 550 | 85.2 | 52.0 |
| 600 | 85.2 | 58.0 |

EXAMPLE 12B

In a similar manner, ethylation of toluene was accomplished utilizing a feed stream of toluene (WHSV=7.0) and ethylene (WHSV=0.5) in the presence of the P-ZSM-5 catalyst at 400° C. Conversion of toluene was 74.8% and selectivity to the para-isomer of ethyltoluene was 55.5%.

EXAMPLE 13

[Disproportionation reaction with P-modified zeolite]

Toluene disproportionation was tested by passing a stream of toluene over the P-ZSM-5 catalyst of Example 11 at a feed WHSV of 3.5 and at temperatures of between 475° and 550° C. The results are summarized as follows:

| Temperature °C. | Toluene Conv. % | % Selectivity, Mole | | % Para in Xylenes |
|---|---|---|---|---|
| | | Benzene | Xylene | |
| 475 | 14.9 | 52.8 | 47.6 | 39.1 |
| 500 | 27.1 | 53.3 | 45.4 | 35.1 |
| 525 | 37.4 | 56.1 | 42.2 | 32.1 |

-continued

| Temperature °C. | Toluene Conv. % | % Selectivity, Mole | | % Para in Xylenes |
|---|---|---|---|---|
| | | Benzene | Xylene | |
| 550 | 44.0 | 60.4 | 37.3 | 30.1 |

EXAMPLE 14

[Preparation of Sn-P-modified zeolite]

Six grams of the P-modified ZSM-5 of Example 11 were added to a solution of 3.0 g of metallic tin in 15 ml of concentrated HCl at ambient temperature. After 16 hours the mixture was filtered and the zeolite dried at about 90° C. followed by calcining for 3 hours at 500° C. to yield 5.1 g of Sn-P-ZSM-5. Analysis showed the modified zeolite to contain 14.6 wt. % tin and 1.32 wt. % phosphorus.

EXAMPLE 15A

[Alkylation reaction with Sn-P-modified zeolite]

Alkylation of toluene with methanol was carried out by passing a toluene/methanol mixture (molar ratio=4/1) over 1.1 g of the Sn-P-ZSM-5 catalyst prepared in Example 14. The feed WHSV was 10 and the reactor temperature was maintained at 400° C. Toluene conversion was 29.2% with a selectivity to the para-isomer of xylene of 71.5%. By comparison, the unmodified zeolite showed only 24.4% selectivity to the para-isomer under similar conversion conditions (Example 1A) while the P-modified ZSM-5 provided only 66.6% selectivity (Example 12A).

EXAMPLE 15B

Toluene and ethylene were reacted in the presence of the Sn-P-ZSM-5 by passing the reactants over the catalyst at WHSV of 7.0 and 0.5, respectively, and 400° C. Conversion of toluene was 47.9% and selectivity to the para-isomer in the ethyltoluene produced was 80.6%. This is a significant increase over the 55.5% selectivity for the P-ZSM-5 of Example 12B.

EXAMPLE 16

[Disproportionation reaction with Sn-P-modified zeolite]

Disproportionation of toluene to benzene and xylenes were accomplished by passing a toluene feed over the Sn-P-modified ZSM-5 of Example 14 at 500° C. and feed WHSV of 3.5. Toluene conversion was 7.1% and selectivity to the para-isomer of xylene was 33.8%.

EXAMPLE 17

Preparation of Pb-P-modified zeolite]

Added 6.0 g of the P-modified zeolite prepared in Example 11 to a solution of 5.0 g lead acetate in 10 ml H₂O at about 80° C. The mixture was maintained at 80°–90° C. for 2 hours, then filtered and the zeolite dried at 90° C. After calcining at 500° C. for 1.2 hours 7.33 g of Pb-P-ZSM-5 were recovered. Analysis showed the lead content of the modified zeolite to be 21.1% and that of phosphorus to be 3.02%.

EXAMPLE 18A

[Alkylation reaction with Pb-P-modified zeolite]

Alkylation of toluene with methanol was carried out in the presence of the Pb-P-ZSM-5 zeolite of Example 17. The toluene/methanol feed stream (4/1 molar ratio) was brought into contact with the modified zeolite at WHSV of 10 and a temperature of 500° C. Toluene conversion was 17.6% and selectivity to the para-isomer of xylene was 94.5%, in comparison to a 53.7% selectivity obtained with the P-ZSM-5 alone (Example 12A).

EXAMPLE 18B

Ethyltoluene was produced by alkylation of toluene with ethylene in the presence of the Pb-P-ZSM-5 zeolite. Reactor temperature was 400° C. and the reactant feed rate (WHSV) was 7.0 for toluene and 0.5 for ethylene. Conversion of toluene was 4.6% and selectivity to para-ethyltoluene was 98%. This is in comparison to a para-selectivity of 55.5% for the P-modified ZSM-5 under the same conditions of reaction (Example 12B).

EXAMPLE 19

[Disproportionation reaction with Pb-P-modified zeolite]

Toluene disproportionation was carried out by passing a toluene feed over a sample of the Pb-P-modified ZSM-5 of Example 17. The reactor temperature was maintained at 550° C. and the toluene feed rate (WHSV) was 3.5. Conversion of toluene was 4.1% with a selectivity of 91.4% to the para-isomer of xylene. Under similar conditions of reaction, the P-ZSM-5 zeolite gave only 30.1% selectivity to the para-isomer.

EXAMPLE 20

[Preparation of Ge-P-modified zeolite]

Five grams of a P-modified ZSM-5 zeolite, similar to that described in Example 11, were mixed with 25.0 g of GeCl₄ and the mixture gently refluxed for 18.25 hours. After cooling, the zeolite was removed by filtration and placed in an oven at 60° C. The temperature was gradually increased to 250° C. over a period of 1 hour and then held at 250° C. for 2 hours. The dried Ge-P-ZSM-5 was then calcined at 500° C. for 2 hours. Germanium content of the modified zeolite was 2.96 wt. % and phosphorus was 3.34 wt. %.

EXAMPLE 21A

[Alkylation reaction with Ge-P-modified zeolite]

Toluene was alkylated with methanol by passing a feed stream of toluene and methanol (molar ratio=4/1) over 2.2 g of the Ge-P-ZSM-5 zeolite of Example 20. The feed WHSV was 11 and the reactor temperature was varied between 400° C. and 600° C. The results obtained at various temperatures are summarized below:

| Temperature °C. | Toluene conv., % | % Para-isomer in Xylenes |
|---|---|---|
| 400 | 42.0 | 80.8 |
| 500 | 62.8 | 72.0 |
| 600 | 78.4 | 70.5 |

Under similar reaction conditions, the ZSM-5 which had been modified with only phosphorus demonstrated a para-selectivity of 52–67% (Example 12A).

EXAMPLE 21B

In a similar manner, toluene and ethylene were reacted in the presence of the Ge-P-ZSM-5 to produce ethyltoluenes. Reaction temperature was 400° C. and the feed WHSV was 7.8 and 0.5, respectively. Conversion of toluene was 88% while selectivity to the para-isomer in the ethyltoluene product was 84.1%.

EXAMPLE 22

[Disproportionation reaction with Ge-P-modified zeolite]

Toluene disproportionation to benzene and xylenes was carried out by passing a toluene feed over the Ge-P-ZSM-5 zeolite of Example 20 at WHSV of 3.5 and temperatures of between 450° C. and 600° C. The results are summarized as follows:

| Temperature °C. | Toluene conv., % | Selectivity, % | | % Para in Xylenes |
|---|---|---|---|---|
| | | Benzene | Xylene | |
| 450 | 4.0 | 45.6 | 54.0 | 54.4 |
| 500 | 9.8 | 44.4 | 55.2 | 49.9 |
| 550 | 19.5 | 45.8 | 53.8 | 45.4 |
| 600 | 28.4 | 49.4 | 49.3 | 43.7 |

EXAMPLE 23

[Disproportionation reaction with unmodified ZSM-11]

A 1.0 g portion of unmodified ZSM-11 zeolite (silica to alumina mole ratio=70) was placed in a quartz flow reactor and heated to temperature. Toluene was passed over the zeolite at WHSV of 3.8 and various temperatures between 400° C. and 600° C. The results are as follows:

| Temperature °C. | Toluene Conv. mole % | % Selectivity, moles | | % Para in Xylene Products |
|---|---|---|---|---|
| | | Benzene | Xylenes | |
| 400 | 3.0 | 51.7 | 47.8 | 24.3 |
| 450 | 8.7 | 48.1 | 50.7 | 24.1 |
| 500 | 21.7 | 49.0 | 48.9 | 23.7 |
| 550 | 39.1 | 53.7 | 42.6 | 23.7 |
| 600 | 49.9 | 58.6 | 36.8 | 23.4 |

EXAMPLE 24A

[Alkylation reaction with unmodified ZSM-11]

A toluene/methanol feed stream, having a 4/1 molar ratio of the respective reactants, was passed over unmodified HZSM-11 zeolite ($SiO_2/Al_2O_3=70$) at 400°–600° C. and a feed WHSV of 10. The results are shown below:

| Temperature °C. | Percent Toluene Conversion | Percent Para Xylene in Xylenes |
|---|---|---|
| 400 | 67.6 | 23.4 |
| 500 | 90.4 | 24.0 |
| 600 | 157.2 | 22.7 |

EXAMPLE 24B

A toluene/ethylene feed stream was similarly brought into contact with the unmodified HZSM-11. The feed WHSV was 7.5 and 0.55, respectively, and the temperature of reaction 400°–450° C. The results are summarized below:

| Temperature °C. | % Toluene Conversion | Isomer ratios of Ethyltoluene | | |
|---|---|---|---|---|
| | | p | m | o |
| 400 | 80.2 | 27.3 | 58.4 | 14.3 |
| 450 | 81.9 | 27.2 | 57.9 | 14.9 |

EXAMPLE 25

Preparation of Pb-modified ZSM-11]

Added 1.5 g of HZSM-11 zeolite ($SiO_2/Al_2O_3$ ratio=70) to a solution of 3.0 g lead acetate in 6 ml $H_2O$ at about 60° C. The mixture was maintained at 80°–90° C. for 1 hour, then filtered and the zeolite dried for 16 hours at 90° C. The dried zeolite was thereafter calcined at 500° C. for 2.0 hours to yield 2.14 g of Pb-ZSM-11. The lead content of the modified zeolite was 36.7 wt. %.

EXAMPLE 26A

[Alkylation reaction with Pb-modified ZSM-11]

Alkylation of toluene with methanol was catalyzed by the Pb-ZSM-11 zeolite of Example 25 by passing a feed stream of toluene and methanol (4/1 molar ratio) over the modified zeolite at feed WHSV of 10 and a reactor temperature of 500° C. Toluene conversion was 52.0% with selectivity to the para-isomer in the xylene product of 42.8%. This in in marked contrast to the 24.0% para-selectivity achieved by the unmodified HZSM-11 under similar conditions of reaction (Example 24A).

EXAMPLE 26B

In a similar manner, ethyltoluene was produced by alkylation of toluene with ethylene in the presence of the Pb-ZSM-11 zeolite of Example 25. The feed WHSV was 3.4 of toluene and 0.5 for ethylene and reactor temperature was 400° C. Conversion of toluene was 5.8% with a 73.9% selectivity to the para-isomer of ethyltoluene.

EXAMPLE 27

[Disproportionation reaction with Pb-modified ZSM-11]

Toluene disproportionation was carried out by contacting a toluene feed with the Pb-ZSM-11 zeolite of Example 25 at 550° C. and WHSV of 3.5. Toluene conversion was 1.2% and selectivity to the para-isomer of xylene was 42.9%.

It is to be understood that the foregoing examples are intended to be merely illustrative of certain specific embodiments of the disclosed invention. As those of skill in the art will readily appreciate, there are many variations which may be made on these specific embodiments without departing from the spirit of the invention described herein and such variations are clearly to be encompassed within the ambit of the following claims.

We claim:

1. A process for conversion of organic compounds, said process comprising contacting said organic compounds with a crystalline zeolite catalyst at a temperature of between about 250° C. and about 750° C. and a pressure within the approximate range of $10^5 N/m^2$ to $10^7 N/m^2$, said zeolite being characterized by a silica to alumina mole ratio of at least 12 and a constraint index within the approximate range of 1 to 12, said zeolite having undergone prior modification by treatment with one or more compounds containing metal elements of Group IVB to deposit thereon at least 0.25 weight percent of such metal element.

2. The process of claim 1 wherein said temperature is between 300° C. and 650° C.

3. The process of claim 1 wherein said metal element of Group IVB is chosen from the group consisting of germanium, tin and lead.

4. The process of claim 1 wherein said metal element is germanium.

5. The process of claim 4 wherein said germanium comprises between 1 and 15 weight percent of the modified zeolite catalyst.

6. The process of claim 1 wherein said metal element is tin.

7. The process of claim 6 wherein said tin comprises between 1 and 25 weight percent of the modified zeolite catalyst.

8. The process of claim 1 wherein said metal element is lead.

9. The process of claim 8 wherein said lead comprises between about 1 and 40 weight percent of the modified zeolite catalyst.

10. The process of claim 1 wherein said zeolite is also modified by treatment thereof with a compound of the element phosphorus to deposit thereon at least 0.25 weight percent of phosphorus.

11. The process of claim 10 wherein said zeolite has deposited thereon both phosphorus and germanium.

12. The process of claim 10 wherein said zeolite has deposited thereon both phosphorus and tin.

13. The process of claim 10 wherein said zeolite has deposited thereon both phosphorus and lead.

14. The process of claim 1 wherein said zeolite is admixed with a binder therefor.

15. The process of claims 1, 2, 3, 4, 5, 6, 7, 8, 9, 10, 11, 12, 13 or 14 wherein said conversion comprises the alkylation of an aromatic compound by contacting said compound with an alkylating agent to produce dialkylbenzene compounds wherein the 1,4-dialkylbenzene isomer is present in excess of its normal equilibrium concentration.

16. The process of claim 15 wherein said zeolite is chosen from the group consisting of ZSM-5, ZSM-11, ZSM-12, ZSM-23, ZSM-35, ZSM-38 and ZSM-48.

17. The process of claim 15 wherein said zeolite is ZSM-5.

18. The process of claim 15 wherein said zeolite is ZSM-11.

19. The process of claims 1, 2, 3, 4, 5, 6, 7, 8, 9, 10, 11, 12, 13 or 14 wherein said conversion comprises the transalkylation of aromatic compounds to produce dialkylbenzene compounds wherein the 1,4-dialkylbenzene isomer is present in excess of its normal equilibrium concentration.

20. The process of claim 19 wherein said zeolite is chosen from the group consisting of ZSM-5, ZSM-11, ZSM-12, ZSM-23, ZSM-35, ZSM-38 and ZSM-48.

21. The process of claim 19 wherein said zeolite is ZSM-5.

22. The process of claim 19 wherein said zeolite is ZSM-11.

23. The process of claims 1, 2, 3, 4, 5, 6, 7, 8, 9, 10, 11, 12, 13 or 14 wherein said conversion comprises disproportionation of alkylbenzenes to produce benzene and dialkylbenzenes in which the proportion of 1,4-dialkylbenzene isomer is in excess of its normal equilibrium concentration.

24. The process of claim 23 wherein said zeolite is chosen from the group consisting of ZSM-5, ZSM-11, ZSM-12, ZSM-23, ZSM-35, ZSM-38 and ZSM-48.

25. The process of claim 23 wherein said zeolite is ZSM-5.

26. The process of claim 23 wherein said zeolite is ZSM-11.

* * * * *